(12) United States Patent
Ta et al.

(10) Patent No.: US 8,628,565 B2
(45) Date of Patent: Jan. 14, 2014

(54) INTRAVASCULAR STENT

(75) Inventors: Diem Uyen Ta, San Jose, CA (US); Timothy A. Limon, Cupertino, CA (US); Andy E. Denison, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 956 days.

(21) Appl. No.: 11/104,862

(22) Filed: Apr. 13, 2005

(65) Prior Publication Data
US 2006/0235506 A1  Oct. 19, 2006

(51) Int. Cl.
*A61F 2/86* (2013.01)

(52) U.S. Cl.
USPC .................. 623/1.16; 623/1.15; 623/1.42

(58) Field of Classification Search
USPC ............ 623/1.15–1.16, 1.17, 23.7, 1.1, 1.11, 623/1.12, 1.13, 1.14, 1.18, 1.19, 1.2, 1.21, 623/1.3, 1.31, 1.42
See application file for complete search history.

(56) References Cited

U.S. PATENT DOCUMENTS

| | | | |
|---|---|---|---|
| 4,241,146 A | 12/1980 | Suvacebju et al. | |
| 4,725,334 A | 2/1988 | Brimm | |
| 4,728,328 A | 3/1988 | Hughes et al. | |
| 4,733,665 A | 3/1988 | Palmaz | |
| 4,739,762 A | 4/1988 | Palmaz | |
| 4,762,128 A | 8/1988 | Rosenbluth | |
| 4,776,337 A | 10/1988 | Palmaz | |
| 4,830,003 A | 5/1989 | Wolff et al. | |
| 4,893,623 A | 1/1990 | Rosenbluth | |
| 4,986,831 A | 1/1991 | King et al. | |
| 5,019,090 A | 5/1991 | Pinchuk | |
| 5,064,435 A | 11/1991 | Porter | |
| 5,102,417 A | 4/1992 | Palmaz | |
| 5,108,417 A | 4/1992 | Sawyer | |
| 5,133,732 A | 7/1992 | Wiktor | |
| 5,135,536 A | 8/1992 | Hillstead | |
| 5,195,984 A | 3/1993 | Schatz | |
| 5,282,823 A | 2/1994 | Schwartz et al. | |
| 5,344,425 A | 9/1994 | Sawyer | |
| 5,354,308 A | 10/1994 | Simon et al. | |
| 5,383,892 A | 1/1995 | Cardon et al. | |
| 5,395,390 A | 3/1995 | Simon et al. | |
| 5,413,597 A | 5/1995 | Krajicek | |
| 5,421,955 A | 6/1995 | Lau et al. | |
| 5,449,373 A | 9/1995 | Pinchasik et al. | |
| 5,527,324 A | 6/1996 | Krantz et al. | |

(Continued)

FOREIGN PATENT DOCUMENTS

| | | |
|---|---|---|
| DE | 195 37 872 A | 4/1997 |
| EP | 0 201 466 A | 11/1986 |

(Continued)

*Primary Examiner* — David Isabella
*Assistant Examiner* — Suba Ganesan
(74) *Attorney, Agent, or Firm* — Fulwider Patton LLP

(57) ABSTRACT

An expandable stent for implantation in a body lumen, such as an artery, is disclosed. The stent consists of a plurality of radially expandable cylindrical rings generally aligned on a common longitudinal stent axis and interconnected by one or more interconnecting links placed so that the stent is flexible in the longitudinal direction. The link pattern is optimized to reduce strain on the links and enhance longitudinal flexibility and security of the stent. The stent includes a distal end ring and a proximal end ring that have a length that is shorter than the length of the body rings.

15 Claims, 7 Drawing Sheets

(56) References Cited

U.S. PATENT DOCUMENTS

| | | |
|---|---|---|
| 5,569,295 A | 10/1996 | Lam |
| 5,591,197 A * | 1/1997 | Orth et al. .................... 623/1.16 |
| 5,601,593 A | 2/1997 | Freitag |
| 5,607,442 A | 3/1997 | Fischell et al. |
| 5,630,829 A | 5/1997 | Lauterjung |
| 5,636,641 A | 6/1997 | Fariabi |
| 5,681,346 A | 10/1997 | Orth et al. |
| 5,693,089 A | 12/1997 | Inoue |
| 5,707,388 A | 1/1998 | Lauterjung |
| 5,716,393 A | 2/1998 | Linderberg et al. |
| 5,741,327 A | 4/1998 | Frantzen |
| 5,759,192 A | 6/1998 | Saunders |
| 5,776,161 A | 7/1998 | Globerman |
| 5,807,404 A | 9/1998 | Richter |
| 5,810,868 A | 9/1998 | Lashinski et al. |
| 5,827,321 A | 10/1998 | Roubin |
| 5,836,966 A | 11/1998 | St. Germain |
| 5,843,120 A | 12/1998 | Israel et al. |
| 5,868,783 A | 2/1999 | Tower |
| 5,913,895 A | 6/1999 | Burpee et al. |
| 5,922,020 A | 7/1999 | Klein |
| 6,017,365 A * | 1/2000 | Von Oepen .................... 623/1.15 |
| 6,027,526 A | 2/2000 | Limon et al. |
| 6,042,597 A | 3/2000 | Kveen |
| 6,042,606 A | 3/2000 | Frantzen |
| 6,099,561 A | 8/2000 | Alt |
| 6,174,329 B1 | 1/2001 | Callol et al. |
| 6,183,506 B1 | 2/2001 | Penn et al. |
| 6,190,403 B1 * | 2/2001 | Fischell et al. ............... 623/1.16 |
| 6,217,608 B1 | 4/2001 | Penn et al. |
| 6,231,598 B1 | 5/2001 | Berry et al. |
| 6,245,101 B1 | 6/2001 | Drasler et al. |
| 6,270,524 B1 * | 8/2001 | Kim ................ 623/1.15 |
| 6,273,910 B1 | 8/2001 | Cox et al. |
| 6,273,911 B1 | 8/2001 | Cox et al. |
| 6,287,336 B1 | 9/2001 | Globerman |
| 6,364,903 B2 | 4/2002 | Tseng et al. |
| 6,416,539 B1 | 7/2002 | Hassdenteufel |
| 6,416,543 B1 | 7/2002 | Hilaire |
| 6,468,302 B2 | 10/2002 | Cox et al. |
| 6,511,505 B2 | 1/2003 | Cox et al. |
| 6,602,284 B2 | 8/2003 | Cox et al. |
| 6,616,688 B2 | 9/2003 | Von Oepen |
| 6,776,794 B1 * | 8/2004 | Hong et al. .................... 623/1.15 |
| 2002/0058989 A1 * | 5/2002 | Chen et al. .................... 623/1.15 |
| 2004/0002753 A1 * | 1/2004 | Burgermeister et al. .... 623/1.15 |

FOREIGN PATENT DOCUMENTS

| | | |
|---|---|---|
| EP | 0 540 290 A | 5/1993 |
| EP | 0 541 443 A | 5/1993 |
| EP | 0 606 165 | 7/1994 |
| EP | 0 669 114 A1 | 2/1995 |
| EP | 0 679 372 | 11/1995 |
| EP | 0 688 545 A | 12/1995 |
| EP | 0 800 801 A1 | 10/1997 |
| EP | 0 806 190 | 11/1997 |
| EP | 0 669 114 B1 | 6/1998 |
| EP | 1 042 997 A1 | 10/2000 |
| EP | 0 888 093 BI | 7/2001 |
| EP | 1 179 323 A2 | 2/2002 |
| WO | WO 94 17754 | 8/1994 |
| WO | WO 95 23563 | 9/1995 |
| WO | WO 95 26695 | 10/1995 |
| WO | WO 95 33422 | 12/1995 |
| WO | WO 96 03092 A1 | 2/1996 |
| WO | WO 96 09013 | 3/1996 |
| WO | WO 97 32543 | 9/1997 |
| WO | WO 97/40781 | 11/1997 |
| WO | WO 98 22159 | 5/1998 |
| WO | WO 98 58600 | 12/1998 |
| WO | WO 00/28922 | 5/2000 |
| WO | WO 01/89414 A1 | 11/2001 |

* cited by examiner

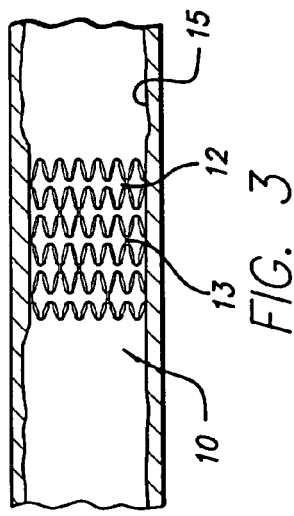
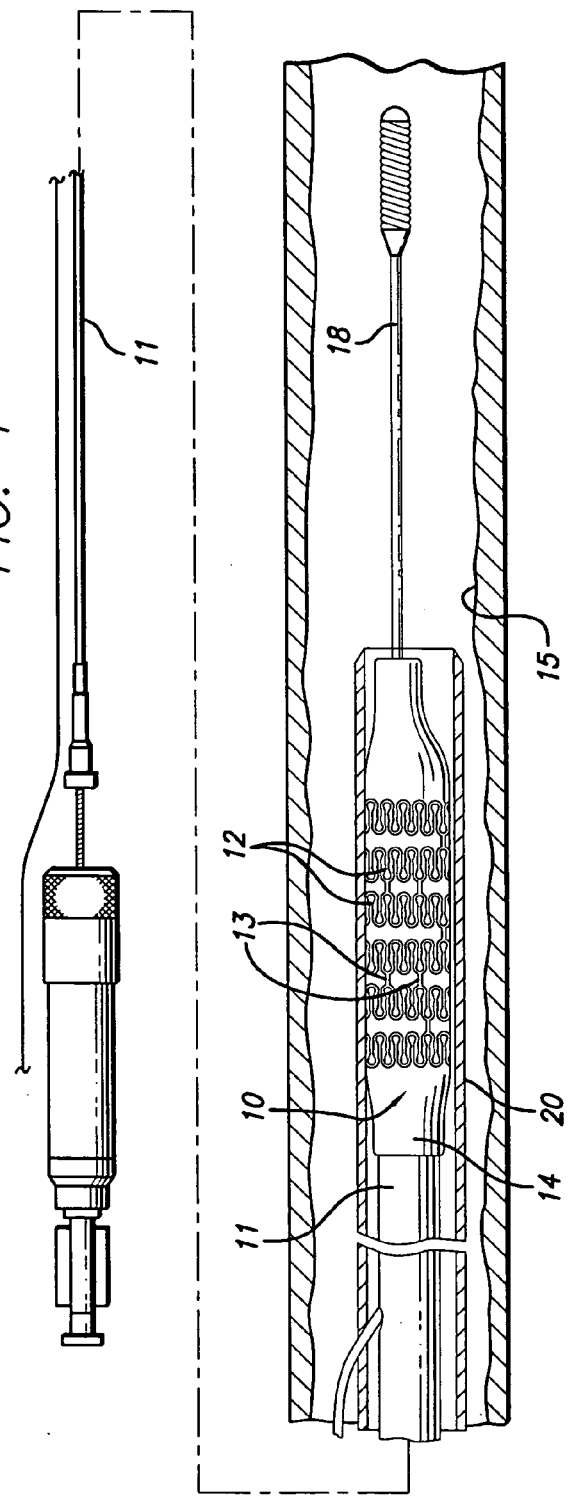
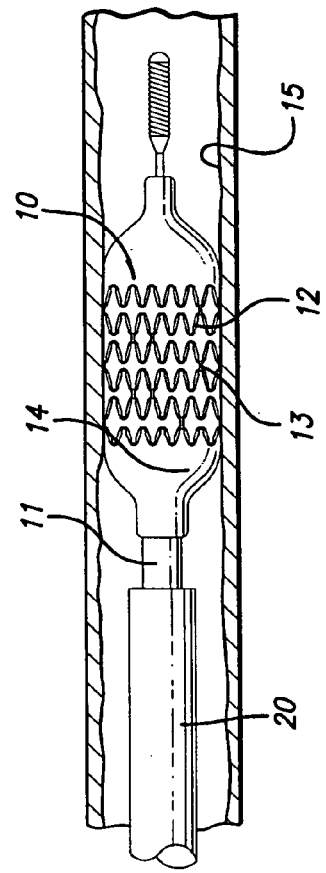

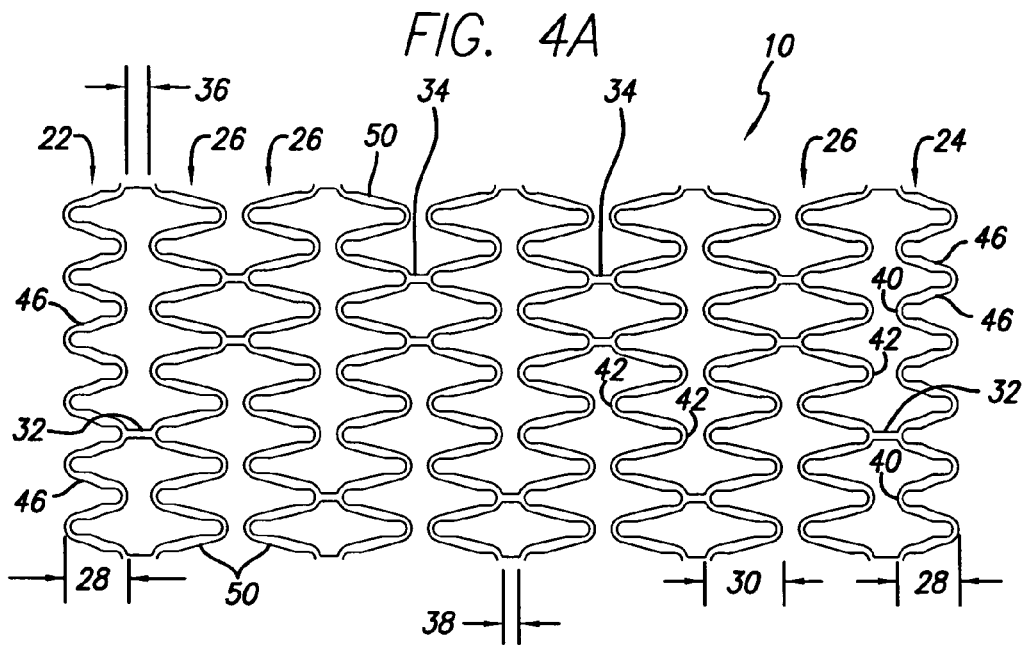
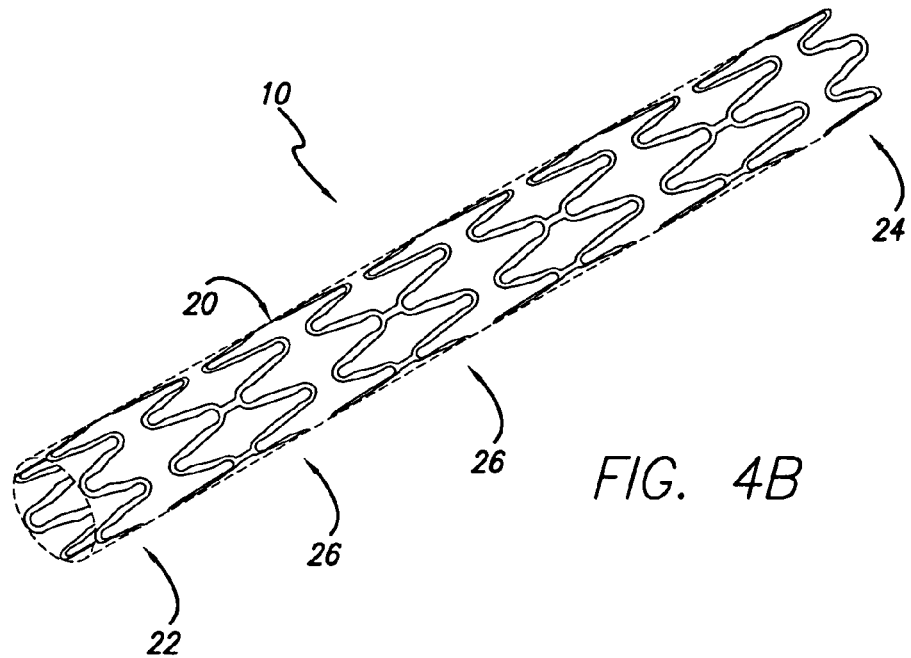

INTRAVASCULAR STENT

BACKGROUND OF THE INVENTION

The present invention relates to expandable endoprosthesis devices, generally known as stents, which are designed for implantation in a patient's body lumen, such as blood vessels to maintain the patency thereof. These devices are particularly useful in the treatment and repair of blood vessels after a stenosis has been compressed by percutaneous transluminal coronary angioplasty (PTCA), percutaneous transluminal angioplasty (PTA), or removed by atherectomy or other means.

Stents are generally cylindrically-shaped devices which function to hold open and sometimes expand a segment of a blood vessel or other lumen such as a coronary artery. They are particularly suitable for use to support the lumen or hold back a dissected arterial lining which can occlude the fluid passageway therethrough.

A variety of devices are known in the art for use as stents and have included a plastically deformable wire mesh in a variety of patterns that are expanded after being placed intraluminally on a balloon catheter; helically wound coiled springs manufactured from an expandable heat sensitive metal; and self-expanding stents inserted in a compressed state and shaped in a zigzag pattern. One of the difficulties encountered using prior art stents involved maintaining the radial rigidity needed to hold open a body lumen while at the same time maintaining the longitudinal flexibility of the stent to facilitate its delivery and accommodate the often tortuous path of the body lumen.

Another problem area has been the limited range of expandability. Certain prior art stents expand only to a limited degree due to the uneven stresses created upon the stents during radial expansion. This necessitates providing stents with a variety of diameters, thus increasing the cost of manufacture. Additionally, having a stent with a wider range of expandability allows the physician to redilate the stent if the original vessel size was miscalculated.

SUMMARY OF THE INVENTION

The present devices are directed to stents of enhanced longitudinal flexibility and configuration which permit the stents to expand radially to accommodate a greater number of different diameter vessels, both large and small, than heretofore was possible. The stents have greater flexibility along their longitudinal axis to facilitate delivery through tortuous body lumens, but remain highly stable when expanded radially, to maintain the patency of a body lumen such as an artery or other vessel when implanted therein. The unique patterns of the stents permit both greater longitudinal flexibility and enhanced radial expansibility and stability compared to prior stents.

Each of the different embodiments of stents of the present invention includes a plurality of adjacent cylindrical rings which are generally expandable in the radial direction and arranged in alignment along a longitudinal stent axis. The cylindrical rings are formed in a variety of serpentine wave patterns transverse to the longitudinal axis and contain a plurality of alternating peaks and valleys. At least one link extends between adjacent cylindrical rings and connects them to one another. These links insure minimal longitudinal contraction during radial expansion of the stent in the body vessel. The links can be positioned in differing configurations or patterns along the stent length to enhance stent retention and eliminate strut fractures.

The resulting stent structures are a series of radially expandable cylindrical rings that are spaced longitudinally close enough so that small dissections in the wall of a body lumen may be pressed back into position against the lumenal wall, but not so close as to compromise the longitudinal flexibility of the stent both when being negotiated through the body lumens in their unexpanded state and when expanded into position. The serpentine patterns allow for an even expansion around the circumference by accounting for the relative differences in stress created by the radial expansion of cylindrical rings.

Each of the stents of the present invention can be readily delivered to the desired lumenal location by mounting it on an expandable member, such as a balloon, of a delivery catheter and passing the catheter-stent assembly through the body lumen to the implantation site. A variety of means for securing the stents to the expandable member of the catheter for delivery to the desired location are available. It is presently preferred to compress or crimp the stent onto the unexpanded balloon. Other means to secure the stent to the balloon include providing ridges or collars on the inflatable member to restrain lateral movement, using bioabsorbable temporary adhesives, or adding a retractable sheath to cover the stent during delivery through a body lumen.

The present stent structure is configured to optimize stent strength by varying the strut geometry along the length of the stent. By making the stent stronger or weaker in different regions of the stent, the properties can be customized to a particular application. The stent properties that could be altered include, but are not limited to, the width of each strut, and/or the length each cylindrical ring at a constant strut radial thickness.

The variation of the strength of the stent affects the manner in which the stent expands. As expected, the wider struts tend not to deform as easily as the narrower struts during expansion, while the longer struts within the longer cylindrical rings are better adapted to deployment in larger diameter vessels. On the other hand, an area with shorter and wider struts in the cylindrical rings tends to have greater radial strength than an area with longer and narrower struts in the cylindrical rings, given both areas having the same surface area.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, depicting a stent mounted on a delivery catheter disposed within a vessel.

FIG. 2 is an elevational view, partially in section, similar to the stent of FIG. 1 wherein the stent is expanded within a vessel.

FIG. 3 is an elevational view, partially in section, showing the stent of FIG. 1 expanded within the vessel after withdrawal of the delivery catheter.

FIG. 4A is a plan view depicting one embodiment of the stent in a flattened configuration and illustrating the differences between the end rings and the body rings.

FIG. 4B is a perspective view of the stent of FIG. 4A in a tubular configuration.

DETAILED DESCRIPTION OF THE PREFERRED EMBODIMENTS

Figure 6:
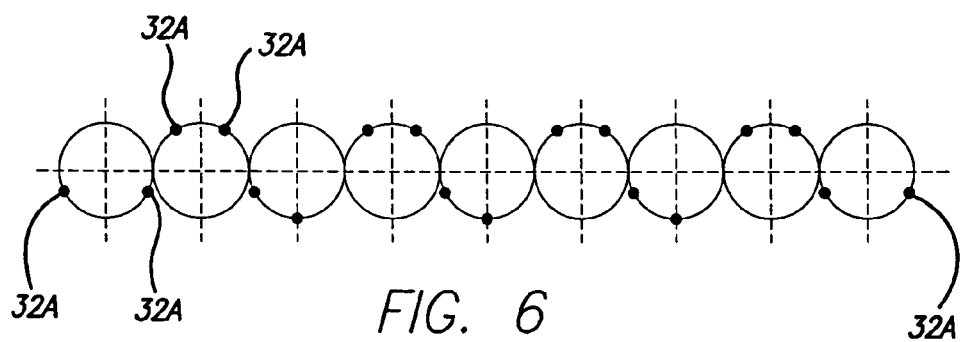
FIG. 6 is a schematic depicting the circumferential relationship of the links along the stent longitudinal axis of the stent of FIG. 5.
Figure 5:
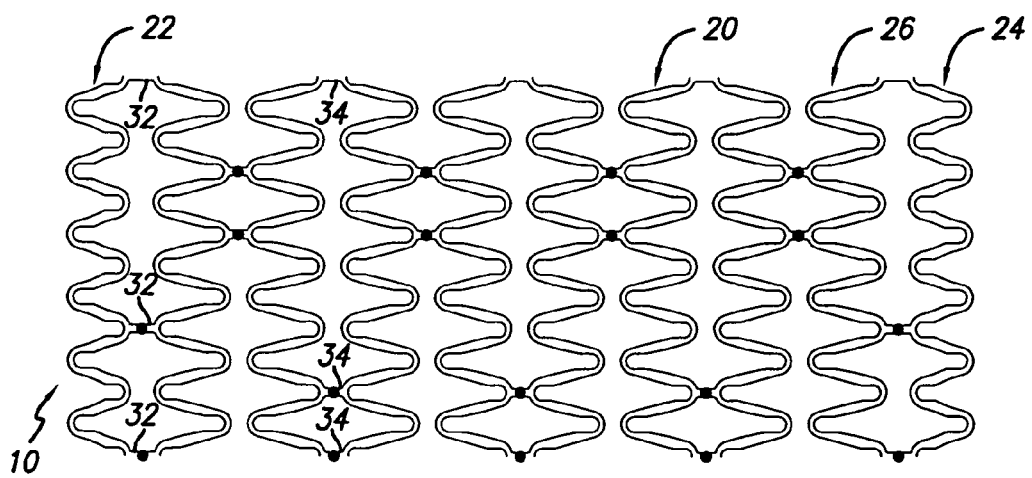
FIG. 5 is a plan view of the stent of FIG. 4A showing the link pattern between the end rings and the body rings.

Prior art stent designs, such as the MultiLink Stent™ manufactured by Advanced Cardiovascular Systems, Inc., Santa Clara, Calif., include plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical ring. A more detailed discussion of the configuration of the MultiLink Stent™ can be found in U.S. Pat. No. 5,569,295 (Lam) and U.S. Pat. No. 5,514,154 (Lau et al.), whose contents are hereby incorporated by reference.

The present invention stent is shown in FIG. 1, where stent 10 is mounted onto delivery catheter 11. Stent 10 generally includes a plurality of radially expandable cylindrical rings 12 disposed generally coaxially and interconnected by links 13 disposed between adjacent cylindrical rings 12. The delivery catheter 11 has an expandable portion or balloon 14 for expanding stent 10 within artery 15 or other vessel.

The delivery catheter 11 onto which stent 10 is mounted is similar to a conventional balloon dilatation catheter for angioplasty procedures. The balloon 14 may be formed of suitable materials such as polyethylene, polyethylene terephthalate, polyvinyl chloride, nylon and, ionomers such as Surlyn® manufactured by the Polymer Products Division of the DuPont Company. Other polymers also may be used.

In order for stent 10 to remain in place on balloon 14 during delivery to the artery 15, stent 10 is compressed or crimped onto balloon 14.

The delivery of stent 10 to a coronary artery for example, is accomplished in the following manner. Stent 10 is first mounted onto inflatable balloon 14 on the distal extremity of delivery catheter 11. Stent 10 may be crimped down onto balloon 14 to obtain a low profile. The catheter-stent assembly can be introduced within the patient's vasculature in a conventional technique through a guiding catheter (not shown). Guidewire 18 is disposed through the arterial section. The catheter-stent assembly is then advanced over guidewire 18 within artery 15. Balloon 14 of catheter 11 is inflated or expanded, thus expanding stent 10 against the inside of artery 15, which is illustrated in FIG. 2. While not shown in the drawing, artery 15 is preferably expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid therethrough.

In general, stent 10 serves to hold open artery 15 after catheter 11 is withdrawn, as illustrated in FIG. 3. Due to the formation of stent 10 from an elongated tubular member, the undulating component of the cylindrical elements of stent 10 is relatively flat in a transverse cross-section so that when stent 10 is expanded, cylindrical rings 12 are pressed into the wall of artery 15. Cylindrical rings 12 of stent 10 that are pressed into the wall of artery 15 will eventually be covered with endothelial cell growth that further minimizes blood flow turbulence. The serpentine pattern of cylindrical rings 12 provide good tacking characteristics to prevent stent movement within the artery.

In one embodiment, shown in FIGS. 4A-7, stent 10 includes a tubular body 20 having a first end ring 22 and a second end ring 24. A number of body rings 26 are positioned between the first end ring and the second end ring. The first end ring and the second end ring each have a first length 28 and the body rings each have a second length 30. The first end ring and the second end ring each are shorter than the body rings for several reasons. First, when the stent is expanded, the stent length, after expansion, remains substantially the same as that prior to expansion, which is desirable for positioning the stent at a precise location in artery 15. By maintaining the overall stent length during expansion there is minimal trauma or injury to the artery in the axial direction from the radial expansion of the stent rings. Secondly, there is a greater gap between the rings which allows the balloon to expand into the stent more during the heat and pressure process performed after the stent has been crimped on the balloon, which improves stent retention on the balloon during delivery.

All of the rings are positioned in an out-of-phase relationship and are connected by links. The first end ring 22 and the second end ring 24 each are connected to adjacent body rings by first links 32. The links extend from a peak 40 of the first end ring to a peak 42 of the adjacent body ring. Likewise, the links extend from peaks 40 of the second end ring to the peaks 42 on an adjacent body ring. Similarly, each of the body rings are attached to adjacent body rings by second links 34. The second links extend from the peak 42 of one body ring to the adjacent peak 42 of an adjacent body ring. The first links have a first length 36 and the second links have a second length 38, where the first length of the first links is greater than the second length of the second links.

The number of links between the first end ring 22 and the body ring 26, and the second end ring 24 and the body ring can vary in order to vary the flexibility of stent 10. In one embodiment, as shown in FIGS. 4A-7, there are two first links 32 between the end rings and the body rings. Further, there are two second links 34 between adjacent body rings. The flexibility of the stent also is affected by the spacing of the links circumferentially around tubular body 20. For example, referring to FIGS. 5 and 6, the first links are separated by two peaks 40 on the end rings. As shown in FIG. 6, the position 32A of first links 32 are shown being circumferentially spaced by approximately 120°. The second links 34, which connect adjacent body rings 26, are separated by one peak 42 on the body rings. Looking at the left side of FIG. 5, for example, the first links are separated from the second links of the adjacent body ring by one-and-one-half peaks of separation in one circumferential direction and one-and-one-half peaks separation in the opposite circumferential direction. Moving in an axial direction from the left side of FIG. 5 toward the right side, the second links of one body ring are separated by two-and-one-half peaks 42 in one circumferential direction and one-and-one-half peaks in the opposite circumferential direction. There are several advantages to the link pattern shown in FIGS. 4A-7. First, with the second links 34 being side by side between adjacent body rings 26, there is less strain on the links during bending since both links are close together. In other words, when the links are separated by three or four peaks, each link is under greater stress during bending than if two links were side by side. Accordingly, one preferred link pattern as disclosed provides the best bending fatigue resistance, the highest flexibility for the preferred stent, and provides the best stent retention on the balloon.

Figure 7:
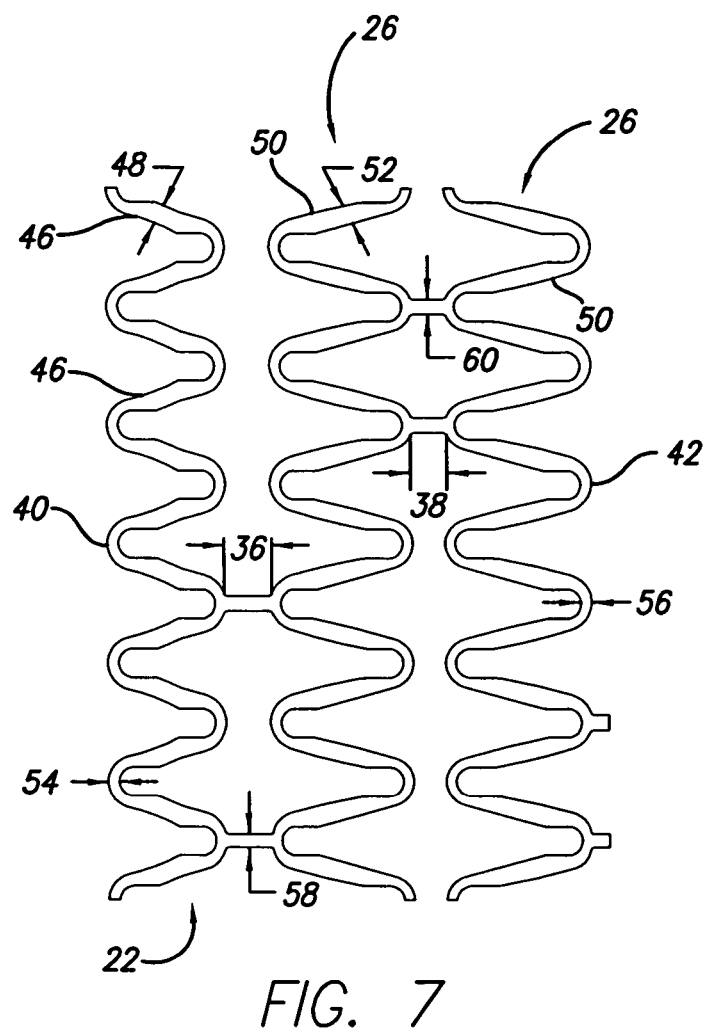
FIG. 7 is a partial plan view of the stent of FIG. 4A depicting the dimensions of the end rings, body rings and links.
Figure 8A:
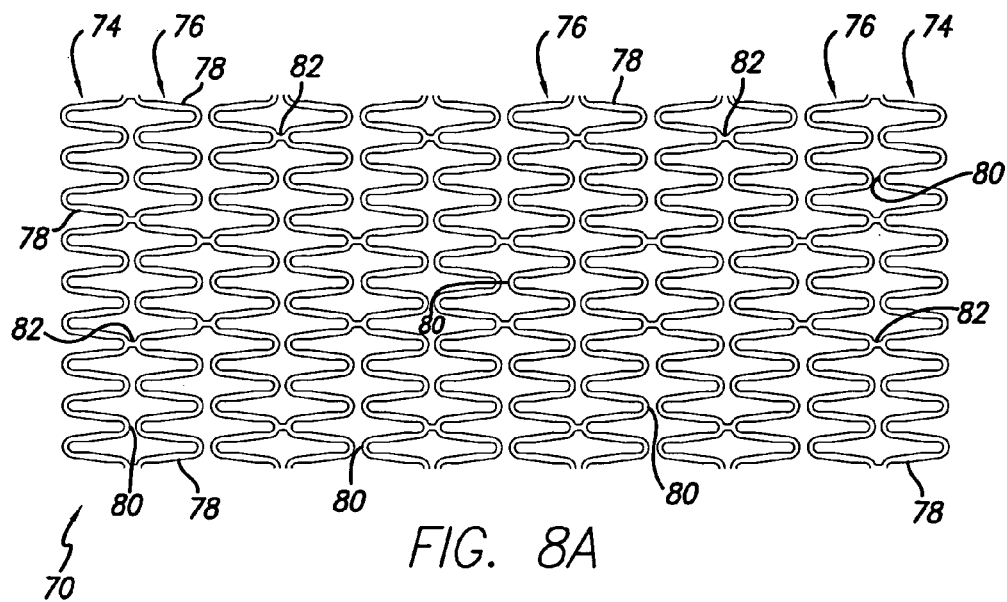
FIG. 8A is a plan view of one embodiment of the stent of the present invention in a flattened configuration depicting the various rings and links.
Figure 8B:
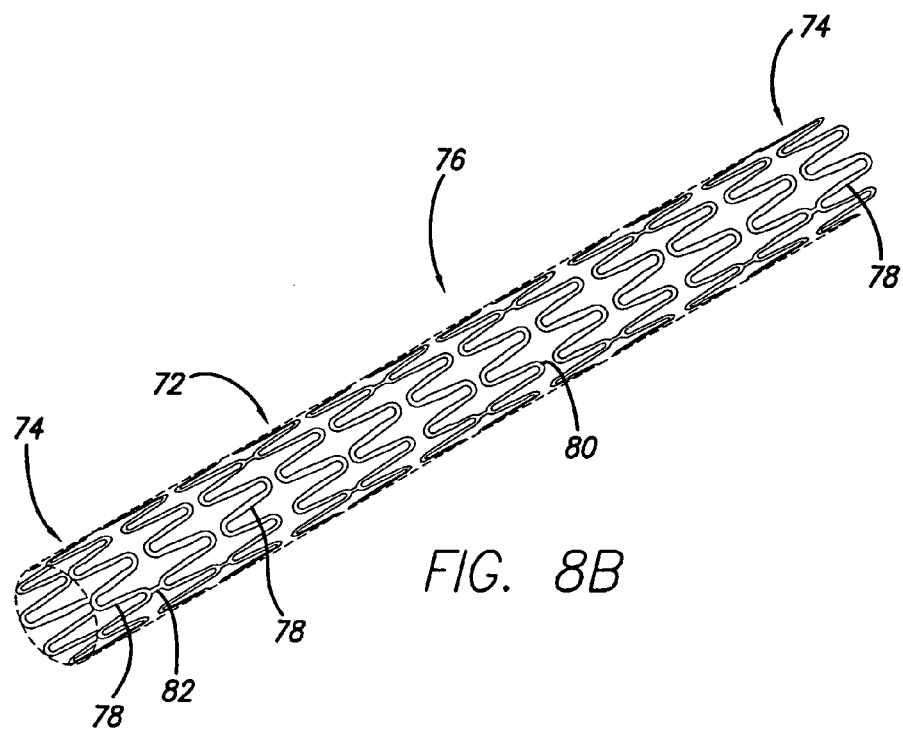
FIG. 8B is a perspective view of the stent of FIG. 8A in a tubular configuration.

With reference to FIG. 7, the first end ring 22 and the second end ring 24 (not shown) each have first bar arms 46 have a first width. In one embodiment, the first bar arm width 48 is approximately 0.0065 inch. The body rings 26 have second bar arms 50 having a second width 52. The width of the second bar arms is approximately 0.0058 inch. Thus, the first bar arms width of 0.0065 inch is greater than the second width of second bar arms of approximately 0.0058 inch. There are several reasons why the end ring bar arms are wider than the body bar arms. First, there is improved stent retention because of better crimping with end rings having wider bar arms since there is less of a tendency for the ends to flare during delivery. The less tendency to flare also reduces strut fractures due to bending fatigue. Also, the shorter, wider bar arms on the end rings have higher radial strength than relatively longer and narrower bar arms. Further, the first end ring 22 and the second end ring 24 are shorter than the body rings 26, so in order to keep the surface area of the end rings the same as the surface area of the body rings, the end rings have wider bar arms. There is less than one percent difference in overall surface area between, for example, first end ring 22 and any of the body rings 26. Likewise, there is less than one percent difference in surface area between the surface area of second end ring 24 and any of body rings 26. In maintaining the surface area among the rings relatively equal, when a drug is applied to the rings, the amount of drug delivered along the length of the stent is more consistent when the surface areas of the rings are substantially equal.

Again referring to FIG. 7, the first end ring 22 and the second end ring 24 have a number of peaks 40 which have first widths 54, that width being approximately 0.0046 inch in one embodiment. The body rings 26 have peaks 42 that have second widths 56, the second width being approximately 0.0038 inch in one embodiment. The first width 54 of the end ring peaks is wider than the second widths 56 of the body ring peaks 42 for substantially the same reasons as stated with respect to the difference in the bar arms widths of the end rings and the body rings.

Referring still to FIG. 7, the first links 32, which extend between the end rings 22, 24 and the body rings 26, have a first width 58 of approximately 0.0042 inch, and a first length 36 of approximately 0.0149 inch. In contrast, the second links 34, which connect adjacent body rings, have a second width 60 of approximately 0.0042 inch, however, the second links are approximately 0.0081 inch in length 38, which is shorter than the length of the first links. By making the first links longer than the second links, while maintaining the width of the links the same, optimum flexibility along the longitudinal axis of the stent is achieved and there is less than 1% difference in surface area between the body rings and end rings.

It is preferred that the stent 10 shown in FIGS. 4A-7, have a constant strut thickness. In one embodiment, the radial thickness of all of the rings and links is approximately 0.0051 inch. While this dimension can vary depending upon the particular application, the 0.0051 inch radial thickness provides optimum flexibility to the stent, conformability to the vessel upon expansion, optimum radiopacity for viewing using fluoroscopy or other means of viewing, and optimum hoop strength in holding the artery open after the stent has been expanded. In this embodiment, there are six peaks 40 in each end ring 22, 24, six peaks 42 for each body ring 26, and the overall stent length is approximately 14 mm (0.5512 inch).

In another embodiment, shown in FIGS. 8A-11, stent 70 includes a tubular body 72 comprised of end rings 74 and body rings 76. There are twelve rings in this embodiment and each ring has nine peaks. As will be further described, the end rings and the body rings have substantially the same dimensions, including overall length, shape, width of bar arms, and width of peaks. Thus, both the end rings and body rings have bar arms 78 that have a constant width of approximately 0.0047 inch. Likewise, the peaks 80 on the end rings and the body rings have a width of approximately 0.0034 inch. Multiple links 82 connect the end rings to the body rings and also connect adjacent body rings to each other, all of which connect at peaks 80. As can be seen from the drawings, all of the rings are out of phase. The link width 84 and the link length 86 are uniform, wherein the width is approximately 0.0041 inch, and the link length is approximately 0.0042 inch. The length 88 of each ring is approximately 0.0606 inch for this embodiment where the overall stent length is 0.5512 inch. The radial thickness of the rings and links is substantially uniform and in this embodiment, is approximately 0.0053 inch. All of the foregoing dimensions and numbers of links and rings are exemplary and intended as one preferred embodiment. Other preferred embodiments may have different dimensions to suit a particular need.

Figure 10:
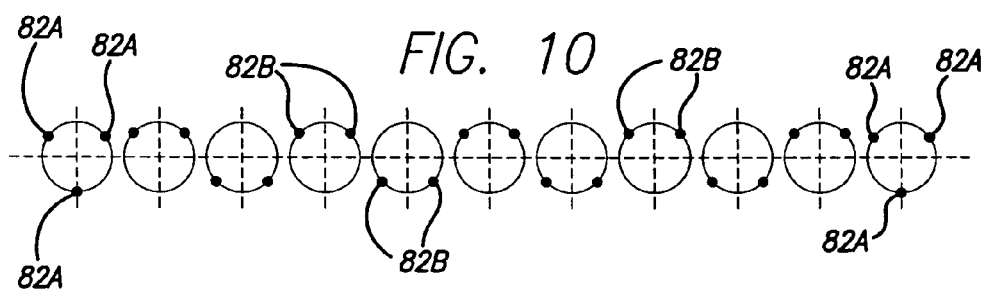
FIG. 10 is a schematic of the link pattern depicted in FIG. 9 showing the circumferential relationship of the links along the stent longitudinal axis.
Figure 9:
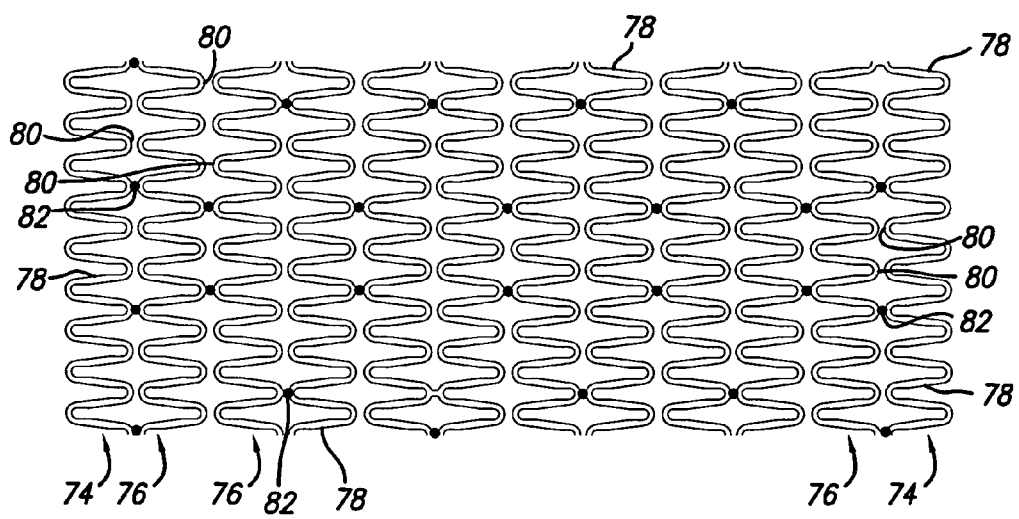
FIG. 9 is a plan view of the stent of FIG. 8A depicting the link pattern.
Figure 11:
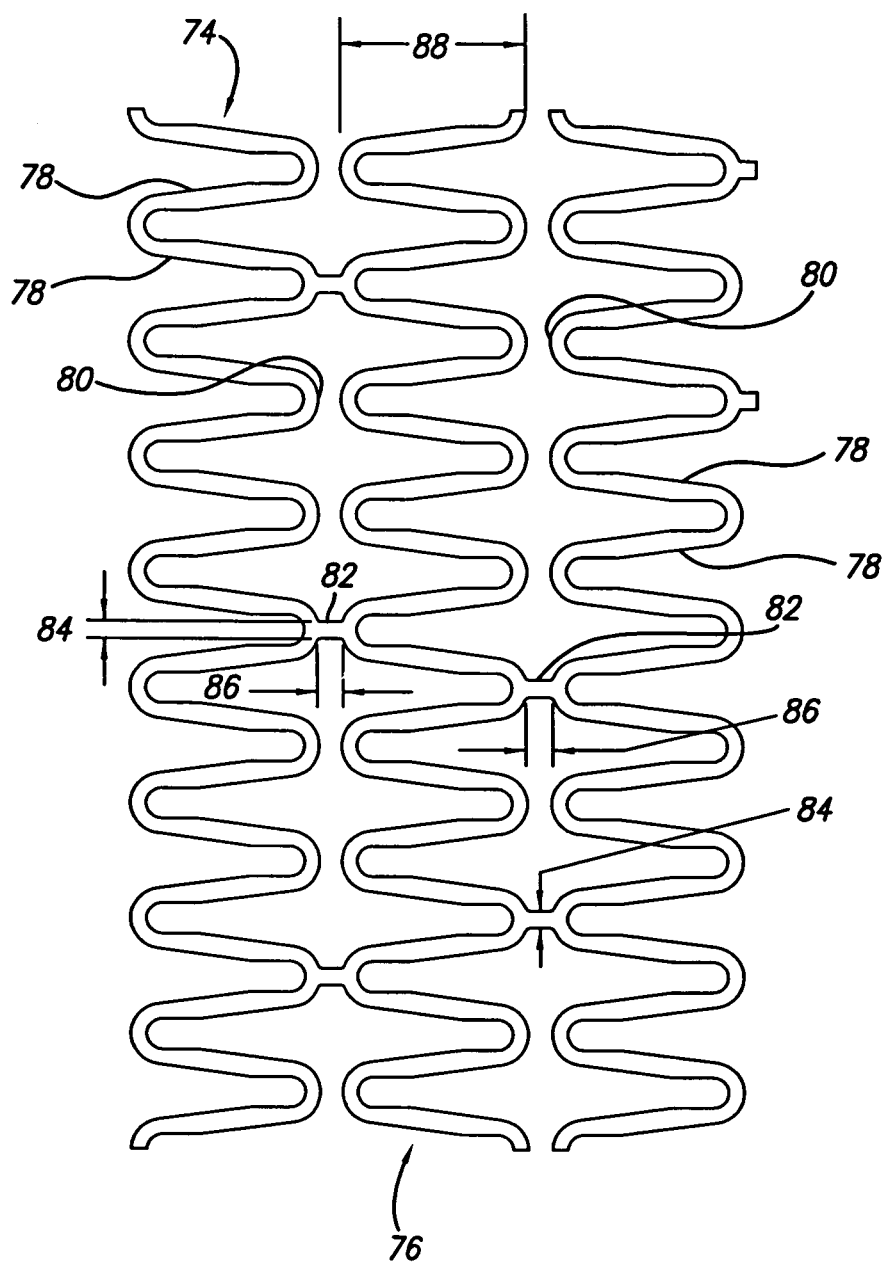
FIG. 11 is a partial plan view of the stent of FIG. 8A depicting the dimensions of the end ring and several body rings.

In order to maximize flexibility, insure that the body of the stent does not turn oval, and the ends of the stent do not flare outwardly during delivery of the stent, the link pattern has been optimized, as can be seen in FIGS. 9 and 10. Thus, in this embodiment, three links 82 connect the end rings 74 to the adjacent body rings 76 while two links connect adjacent body rings to each other. The three links are positioned 82A between the end rings and the body rings are 120° apart as can be seen in FIG. 10. The two links joining adjacent body rings are positioned 82B approximately 80° apart as can be seen in FIG. 10. Moving from the left side of FIG. 9 or FIG. 10 toward the right side, the links 82 joining adjacent body rings have a pattern where the links are separated by two peaks 80, and by seven peaks in the next adjacent set of rings, and then back to two peaks in the next set of adjacent rings toward the right. When viewing FIG. 10, it is clear that the two links joining the adjacent body rings all are separated circumferentially by two peaks 80 in one circumferential direction, and seven peaks 80 in the opposite circumferential direction. This link pattern provides optimal flexibility and security along the longitudinal axis of the stent and also imparts less strain on the links during bending since the links are relatively close together, being separated by only two peaks 80, so that there is less bending stress on each individual link when they are closer together. In this embodiment, there are nine peaks 80 in each of the end rings 74 and body rings 76, and the overall stent length is 14 mm (0.5512 inch).

One important feature of all of the embodiments of the present invention is the capability of the stents to expand from a low-profile diameter to a diameter much greater than heretofore was available, while still maintaining structural integrity in the expanded state and remaining highly flexible. Due to the novel structures, the stents of the present invention can have an overall expansion ratio of about 1.0 up to about 4.0 times the original diameter, or more, using certain compositions of stainless steel. For example, a 316L stainless steel stent of the invention can be radially expanded from a diameter of 1.0 unit up to a diameter of about 4.0 units, which deforms the structural members beyond the elastic limit. The stents still retain structural integrity in the expanded state and will serve to hold open the vessel in which they are implanted. Materials other than stainless steel (316L) may afford higher or lower expansion ratios without sacrificing structural integrity.

The stents of the present invention can be made in many ways. However, the preferred method of making the stent is to cut a thin-walled tubular member, such as a stainless steel tubing, to remove portions of the tubing in the desired pattern for the stent, leaving relatively untouched the portions of the metallic tubing which are to form the stent. It is preferred to cut the tubing in the desired pattern by means of a machine-controlled laser which is well known in the art.

The stent tubing may be made of a suitable biocompatible material such as stainless steel, titanium, cobalt-chromium, tantalum, super-elastic (nickel-titanium) NiTi alloys and even high strength thermoplastic polymers. When stainless steel is utilized, the stainless steel can be annealed and one-eighth hardened. The stent diameters are very small, so the tubing from which it is made must necessarily also have a small diameter. For stents implanted in other body lumens, such as PTA applications, the dimensions of the tubing are correspondingly larger. The diameters and tubing wall thickness of the stents can vary according to a particular application and are known in the art. While it is preferred that the stents be made from laser cut tubing, those skilled in the art will realize that the stent can be laser cut from a flat sheet and then rolled up in a cylindrical configuration with the longitudinal edges welded to form a cylindrical member.

In the instance when the stents are made from plastic, the implanted stent may have to be heated within the arterial site where the stent is expanded to facilitate the expansion of the stent. Once expanded, it would then be cooled to retain its expanded state. The stent may be conveniently heated by heating the fluid within the balloon or the balloon itself directly by a known method.

The stents may also be made of materials such as super-elastic (sometimes called pseudo-elastic) nickel-titanium (NiTi) alloys. In this case, the stent would be formed full size but deformed (e.g. compressed) to a smaller diameter onto the delivery catheter to facilitate intraluminal delivery to a desired intraluminal site. The stress induced by the deformation transforms the stent from an austenite phase to a martensite phase, and upon release of the force when the stent reaches the desired intraluminal location, allows the stent to expand due to the transformation back to the more stable austenite phase. Further details of how NiTi superelastic alloys operate can be found in U.S. Pat. No. 4,665,906 (Jervis) and U.S. Pat. No. 5,067,957 (Jervis), incorporated herein by reference.

The present invention stent is ideally suited for drug delivery (i.e., delivery of a therapeutic agent) since it has a uniform surface area which ensures uniform distribution of drugs. Typically, a polymer is coated onto the stent of the type disclosed in U.S. Pat. Nos. 6,824,559 and 6,783,793 which are incorporated herein by reference.

These bioactive agents can be any agent, which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin, ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The bioactive agents also include metabolites of the foregoing substances and prodrugs of these metabolites. The foregoing substances are listed by way of example and are not meant to be limiting. Other active agents which are currently available or that may be developed in the future are equally applicable.

While the invention has been illustrated and described herein in terms of its use as intravascular stents, it will be apparent to those skilled in the art that the stents can be used in other instances in all vessels in the body. Since the stents of the present invention have the novel feature of expanding to very large diameters while retaining their structural integrity, they are particularly well suited for implantation in almost any vessel where such devices are used. This feature, coupled with limited longitudinal contraction of the stent when it is radially expanded, provides a highly desirable support member for all vessels in the body. Other modifications and improvements may be made without departing from the scope of the invention.

What is claimed:

1. A stent, comprising:
    a tubular body having a first end ring and a second end ring and a plurality of body rings therebetween;
    the end rings and the body rings being positioned in an out-of-phase relationship;
    first links connecting the end rings to the body rings and second links connecting adjacent body rings, wherein only two first links connect the first end ring to an adjacent body ring, only two first links connect the second end ring to an adjacent body ring and only two second links connect adjacent body rings together;
    the first links having a first length and the second links having a second length, the first length being greater than the second length; and
    the first end ring and the second end ring each having a first length that is shorter than a second length of the body rings, wherein the first and second end rings and the body rings have crests, the first and second links extending from a crest on one ring to an axially adjacent crest on an adjacent ring and the only two first links connecting the first end ring to the adjacent body ring are spaced apart by only two crests in one circumferential direction and the only two second links are circumferentially offset from one body ring to the adjacent body ring by one and one-half crests in one circumferential direction and two and one-half crests in the opposite circumferential direction.

2. The stent of claim 1, wherein the first links are linear links.

3. The stent of claim 2, wherein the second links are linear links.

4. The stent of claim 1, wherein each of the first and second end rings have first bar arms having a first width and each of the body rings have second bar arms having a second width.

5. The stent of claim 4, wherein the first width of the first bar arms is greater than the second width of the second bar arms.

6. The stent of claim 1, wherein the first and second end rings have bar arms connected by crests, the bar arms having a width that is greater than a width of the crests.

7. The stent of claim 1, wherein the body rings have bar arms connected by crests, the bar arms having a width that is greater than a width of the crests.

8. The stent of claim 1, wherein the first and second end rings have crests having a first width and the body rings have crests having a second width, the first width being greater than the second width.

9. The stent of claim 1, wherein the stent is formed from metal alloy taken from the group of metal alloys consisting of stainless steel, nickel-titanium, titanium, tantalum, and cobalt-chromium.

10. The stent of claim 1, wherein the stent is formed from annealed stainless steel having one-eighth hardness.

11. The stent of claim 1, wherein the stent is formed from a polymer.

12. The stent of claim 1, wherein each end ring has a first surface area and each body ring has a second surface area, the first surface area being substantially equal to the second surface area.

13. The stent of claim 1, wherein each end ring has a first surface area and each body ring has a second surface area, the difference between the first surface area and the second surface area being less than one percent surface area.

14. The stent of claim 1, wherein the stent is coated with a therapeutic agent.

15. The stent of claim 14, wherein the therapeutic agent used to coat the stent is taken from a group of therapeutic agents consisting of antineoplastic, antimitotic, antiinflammatory, antiplatelet, anticoagulant, antifibrin, antithrombin, antiproliferative, antibiotic, antioxidant, and antiallergic substances, as well as combinations thereof.

* * * * *